United States Patent [19]

Abend et al.

[11] Patent Number: 4,578,999

[45] Date of Patent: Apr. 1, 1986

[54] INSTRUMENT FOR TESTING MATERIALS

[75] Inventors: Klaus Abend, Budingen; Gerhard Huschelrath, Laufach; Wolfgang Bottger, Duisburg; Heinz Schneider, Dusseldorf; Karl Laudenbach, Giessen, all of Fed. Rep. of Germany

[73] Assignees: Mannesmann A.G., Dusseldorf; Nukem GmbH, Hanau, both of Fed. Rep. of Germany

[21] Appl. No.: 287,947

[22] Filed: Feb. 10, 1982

[51] Int. Cl.⁴ ............................................. G01N 29/04
[52] U.S. Cl. ............................................. 73/643
[58] Field of Search ........ 324/228, 232, 233, 236–243, 324/247, 227, 251, 252; 73/643

[56] References Cited

U.S. PATENT DOCUMENTS 4,314,479  2/1982  Spijkerman ............................ 73/643

FOREIGN PATENT DOCUMENTS 0043453  3/1980  Japan .................................... 73/643

OTHER PUBLICATIONS

G. J. Parkinson et al., "Non–Contact Ultrasonics", *British Journal of NDT*, pp. 178–184, Jul. 1977.

Primary Examiner—Stephen A. Kreitman
Attorney, Agent, or Firm—Cushman, Darby and Cushman

[57] ABSTRACT

An instrument for testing of test pieces made of paramagnetic or diamagnetic material as well as of ferromagnetic materials above their Curie point for material defects and/or dimensional accuracy, especially for testing of tubes and slabs above 1000° C. The instrument comprises an electromagnetic transducer (EMT) having magnetic pole shoes and eddy current exciting and receiving windings; and an electronic signal processing unit. The inner pole shoe is conically tapered and fabricated from individual sheets parallel to one another and insulated from each other to prevent the formation of eddy currents that would give rise to undesirable ultrasonic waves that might interfere with the testing process. The pole shoes are positioned so as to develop a magnetic field parallel to the test piece, and the eddy current exciting and receiving windings are heat-insulated with respect to the test piece.

10 Claims, 6 Drawing Figures

INSTRUMENT FOR TESTING MATERIALS

BACKGROUND OF THE INVENTION

This invention provides an instrument for testing paramagnetic and diamagnetic metallic materials, as well as ferromagnetic materials above their Curie points, for material defects and dimensional accuracy. It is particularly useful for testing tubes and slabs above 1000° C. The instrument essentially comprises an electromagnetic transducer (EMT) having two magnetic pole shoes, an eddy current exciting winding, a receiving winding, and an electronic signal processing unit for processing signals from the receiving winding.

In the pursuit of quality control and optimum production efficiency, it is advantageous to test the quality of a product at an early stage of its manufacture so that, in the event that a defect is detected, correction can be made and product will not be wasted. For example, in the manufacture of seamless tubes, especially steel tubes, it is important to test tolerance accuracy while the tube is hot in order to detect erroneous settings of production line equipment while there is still sufficient time to control the roll stands further down the line.

From literature on this subject, it is apparent that many different techniques are known for measuring hot test pieces. These known techniques can be classified into contacting measuring techniques and non-contacting measuring techniques.

One such technique uses an ultrasonic piezoelectric oscillator with a high-pressure flow water coupling. At high pressure a stretch of water is generated between the test piece and the ultrasonic oscillator. The test results achieved with such an arrangement are highly dependent upon the surface quality of the test piece. The test procedure is relatively slow and requires a relatively large quantity of water. Furthermore, the coupling water causes local cooling of the test piece which can cause strains and cracks in the test piece.

Another technique uses piezoelectric oscillators with pressure couplings. Such arrangements permit the direct coupling of the oscillator at high pressure within the range of a roll body. However, such arrangements limit the positioning of the measuring apparatus since measurements cannot be made at any desired point of the train of rollers. Also, it is impossible to take a measurement for tolerance accuracy.

It is also known to excite ultrasonic pulses by using a high capacity pulse laser to locally heat the test piece. However, the use of this instrument for industrial testing is limited.

In addition to the ultrasonic arrangements, it is also known to test materials in production using radiological methods. These methods require working with X-rays, beta rays or gamma rays and therefore present problems of protection from the radiation. Also, radiological testing requires a relatively long measuring time to obtain the accuracy of measurement normally required.

Another known technique is the electrodynamic excitation of ultrasonics. This technique is based on the principle that a force is exerted on a current-carrying body in a magnetic field, acting vertically on the plane that is charged by the magnetic field vector and the current vector. A solenoid generates the magnetic field via a pole shoe configuration while an eddy current pulse is excited in the test piece using a transformer coil. The intensity of the power pulse generated in such a manner and thus the force of the ultrasonic pulse is a function of the magnitude of the eddy current and on the strength of the magnetic field.

In order to be able to generate a sufficiently strong magnetic field and a large eddy current to permit ultrasonic evaluation of the test piece, the EMT head must be positioned very close to the test piece. Depending upon the design of the EMT head itself, different types of ultrasonic waves can be generated. Know methods and instruments are described in the German specification No. 26 55 804 and German application No. 26 21 684 and No. 28 43 804. However, these known instruments have an operational disadvantage. Dependng on its specific design, an EMT head is suitable only for generating transverse waves, guided waves or Lamb-waves, which at high temperatures in the test piece are strongly damped since the shearing module is highly decreasing and thus they cannot be exploited technically. In addition thereto, all of the abovementioned arrangements have the disadvantages that they are restricted to the use of ferritic materials or to such geometries of test pieces that fit between the pole shoes of the EMT. This means that the thickness of the test piece is limited to some millimeters.

The longitudinal wave transducer required for measurements taken on hot test pieces or such made of paramagnetic or diamagnetic metals are described, e.g., in the British Journal of Non-Destructive Testing, 20, 1978, No. 5, September, pages 242 to 247, in Material Evaluation, 34, 1976, No. 4, April pages 81 to 90; and in Ultrasonics, 16, 1978, No. 7, July, pages 151 to 155. However, these publications describe only transducers that are not suitable for use at high temperatures and within small distances of the test piece, as they permit only a maximum test piece temperature of 1000° C.

SUMMARY OF THE INVENTION

It is therefore the object of the present invention to provide an instrument for testing of paramagnetic and diamagnetic metallic materials, as well as of ferromagnetic materials above their Curie points for material defects and dimensional accuracy, and especially for testing tubes and slabs above 1000° C. The test instrument essentially comprises an EMT having two magnetic pole shoes, an eddy current exciting winding, an eddy current receiving winding, and an electronic signal processing unit for processing signals from the eddy current receiving winding. The EMT according to the present invention overcomes the major operational problems associated with prior art devices. Specifically, it generates longitudinal waves, it can be moved within 1 mm of the test piece, and is insensitive to high temperatures.

A primary feature of the EMT is that the pole shoes are designed so as to produce a magnetic field parallel to the test piece. As an additional feature, the eddy current exciting and receiving windings are heat-insulated on their respective sides facing the test piece. These windings, on their respective sides facing the test piece, are embedded in a heat-insulating ceramic layer, and on their respective sides facing away from the test piece are embedded in a heat-conducting ceramic layer.

BRIEF DESCRIPTION OF THE DRAWINGS

The invention will be further described with reference to the following Figures, wherein.

DETAILED DESCRIPTION OF THE PREFERRED EMBODIMENT

Figure 3:
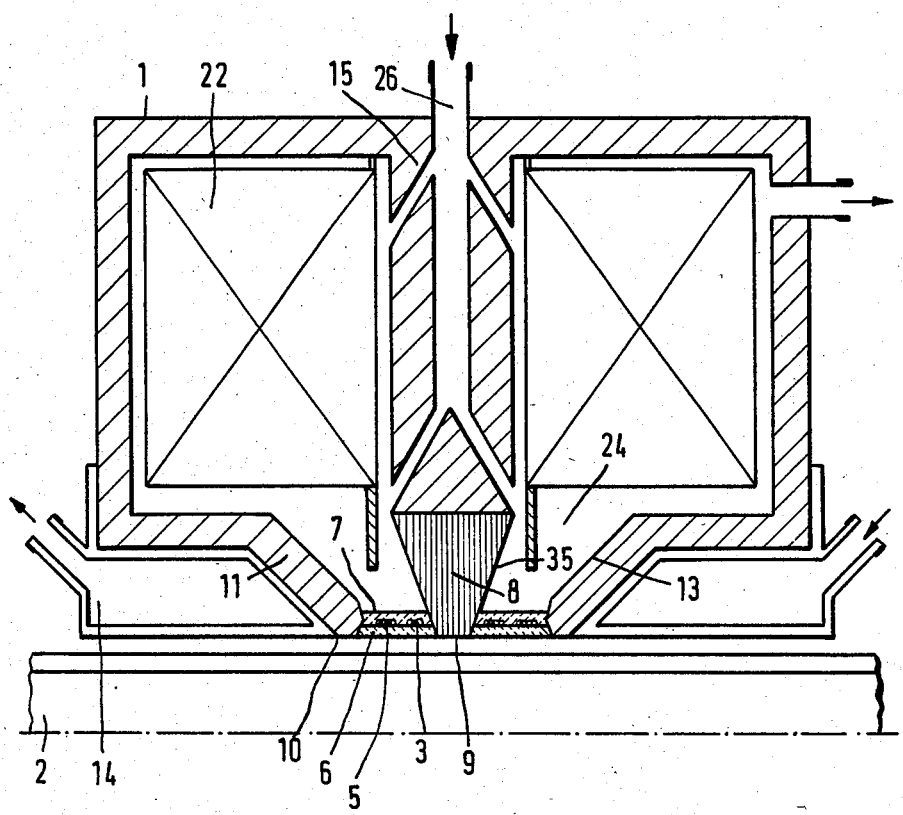
FIG. 3 is a cross-sectional view of transformer 1 shown schematically in FIG. 1.

Referring now to the Figures, the testing and measuring instrument according to the present invention comprises an EMT 1 having a magnetic field exciting winding 22, magnetic pole shoes 8 and 11 (shown in FIG. 3), an eddy current exciting winding 5 and an eddy current receiving winding 3; and an electronic signal processing unit 23.

Eddy current exciting winding 5 and receiving winding 3 are made heat-resistant thereby permitting their placement within a mm of a hot test piece 2. To provide this heat resistance, there is provided a heat-insulating protective ceramic layer 6 (shown in FIG. 3) of, e.g., a thickness of approximately 0.5 mm, preferably of aluminum oxide, on the sides of windings 3 and 5 facing the test piece. Even in the extreme case of a test piece temperature of 1300° C., the temperature on the EMT will not exceed approximately 350° C. The insulated wire, e.g., copper wire, used for the windings 3 and 5, can withstand a continuous heat load up to approximately 200° C. A heat-conducting ceramic layer 7 is applied to that side of each winding facing the EMT (facing away from hot test piece 2), to further cool the windings so that the continuous heat loading capacity will not be exceeded. Ceramic layer 7 provides heat conduction and preferably seals the gap to pole shoes 8 and 11 that is required by the expansiveness of heat-insulating ceramic layer 6. In the preferred embodiment, layer 7 is formed by a heat-conducting ceramic bonding agent. The surface of windings 3 and 5 facing the transformer is preferably additionally cooled by means of a cooling liquid flowing through a cooling liquid passage 24 (see FIG. 3).

Figure 5:
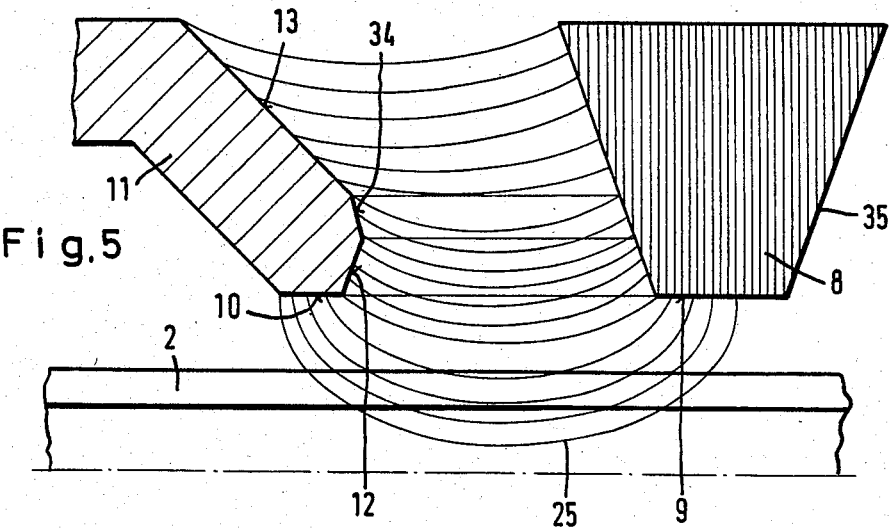
FIG. 5 is a further expanded view of a portion of the transformer shown in FIG. 3 and illustrating a magnetic field generated by the transformer.

In addition to the heat-insulation of the windings 3 and 5, the design of pole shoes 8 and 11 is very important. In order to be able to excite longitudinal waves in the test piece, one must generate a rather strong magnetic field 25 (shown in FIG. 5) parallel to the surface of the test piece. Within the range of the eddy currents only horizontal components are desired. Vertical components excite transverse waves which in hot test pieces do not propagate and cause disturbing echoes when cold paramagnetic and diamagnetic materials are used. Therefore, in order to obtain a field as shown in FIG. 5, it is especially preferably to make one pole shoe 8 (pole shoe 8) of conical design. The angle of conical surface 35 is determined by the width required for eddy current exciting winding 5 and eddy current receiving winding 3. In order to obtain a symmetric magnetic field independent of the distance between transformer 1 and test piece 2, it is desirable that the surface 9 of pole shoe 8 be positioned parallel to the test piece, and be approximately of the same size as the corresponding surface 10 of the counter-pole shoe 11. It is also desirable to incline the pole shoe 11 against the plane of the pole shoe surfaces 9 and 10 at an angle α of at least 20°.

Figure 4:
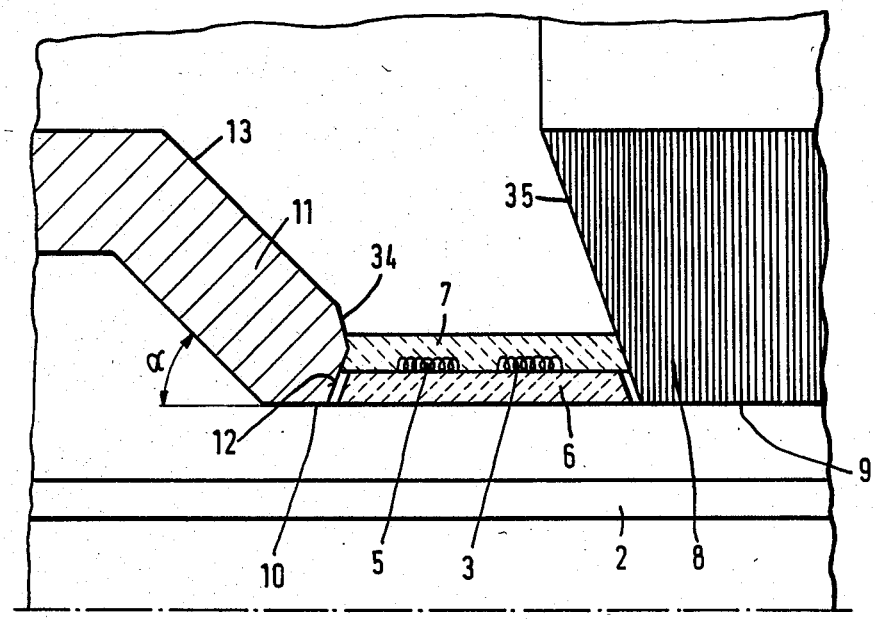
FIG. 4 is an expanded view of a portion of the transformer shown in FIG. 3.
Figure 6:
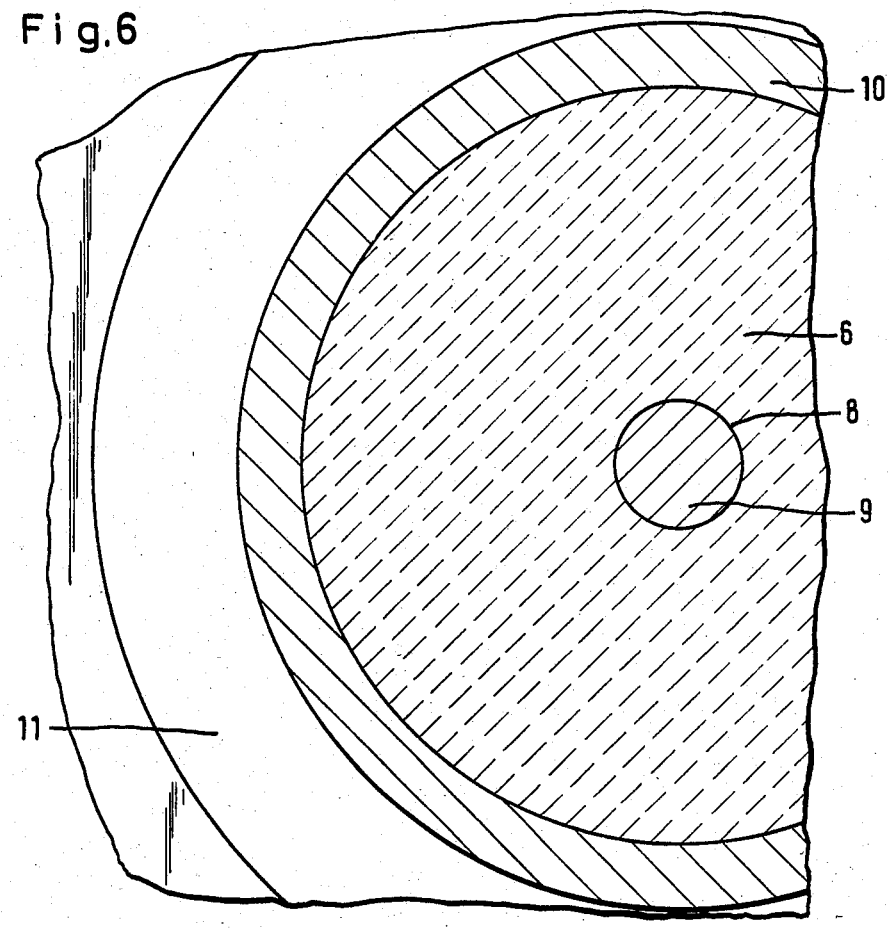
FIG. 6 is a sectional view of FIG. 5.

The inclination of the edge surface 12 of pole shoe 11 should preferably correspond to approximately the angle of the conical surface 35 of pole shoe 8. In order to prevent a substantial loss of field strength, the edge formed by the surface 13 (see FIG. 4) of pole shoe 11 and it edge surface 12 is broken so as to define an edge surface 34. Using this design, it is possible to avoid an especially powerfully developed magnetic field at this place that would otherwise be formed due to the point effect (by reducing the distance).

Special importance must be attached to the construction and inclination of the pole shoes 8 and 11 for another reason. In order to avoid the eddy currents induced by he windings 3 and 5 in the pole shoes 8 and 11, that could lead to ultrasonic pulses in the pole shoes that could return again and again to their places of origin by multiple reflection or appear as set noise in the receiver, it is preferable to choose the inclination angle of pole shoe 11 in such a manner that these interfering impulses will flow outwardly along pole shoe 11. Pole shoe 8 is preferably formed from sheets insulated from each other. This also results in an expansion of the tolerance range for the distance between transformer 1 and test piece 2.

To protect pole shoes 8 and 11 from heat so that the pole shoe material will keep its functional properties below its Curie point, the pole shoes are cooled. Pole shoe 11 preferably has a cooler 14 (see FIG. 3) of non-ferritic material, through which a cooling agent flows. Pole shoe 8, on the other hand, is provided with a cooling channel 26 (see FIG. 3), passing a cooling agent also along heat-conducting ceramic layer 7 and magnetic field exciting winding 22, and in that manner providing for the cooling of these members. The cooling agent is pumped in a closed or open loop system by a pump 27 (see FIG. 1) through EMT 1.

Figure 1:
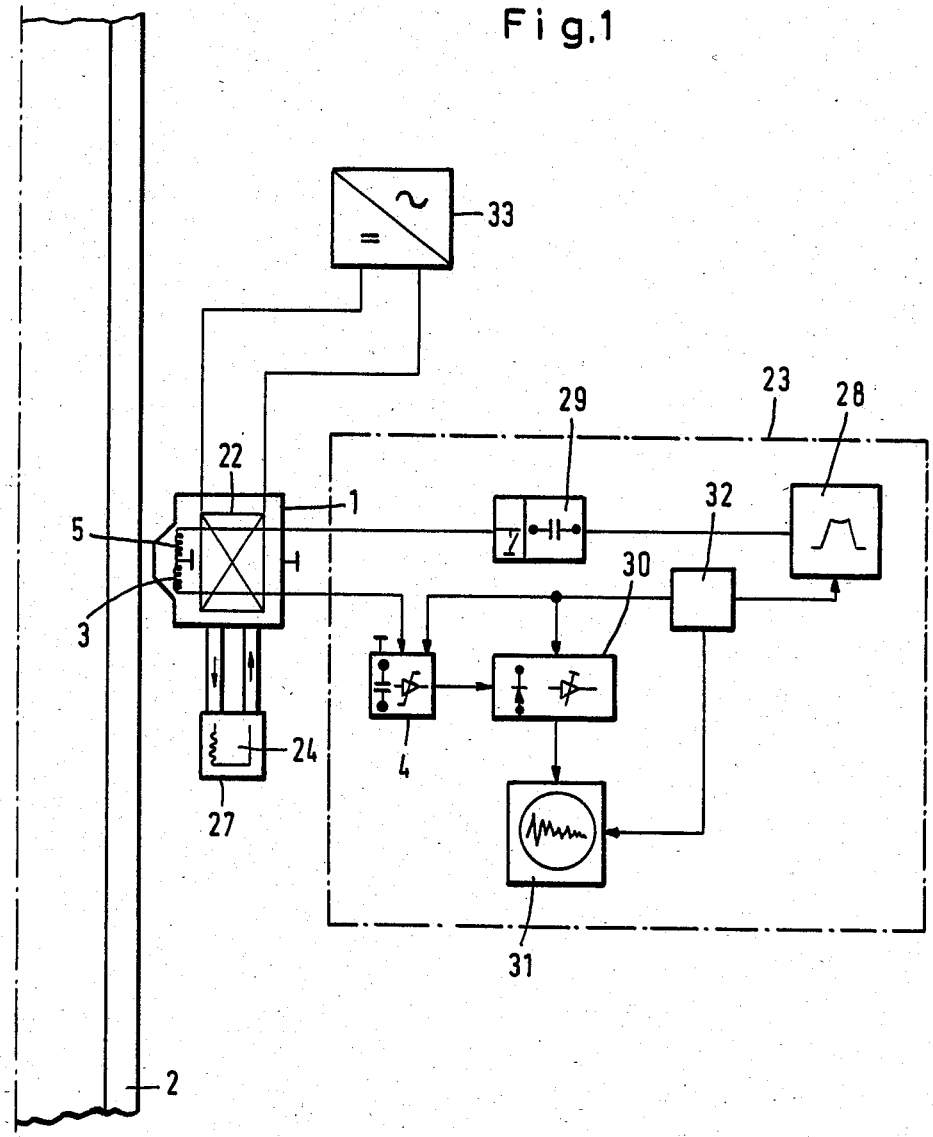
FIG. 1 is a schematic block diagram of the test instrument according to the present invention.

Referring now specifically to FIG. 1, there is shown in schematic and block diagram form the electrical construction of the instrument according to the invention. To generate the ultrasonic pulses, a transmitter 28 via an adapter means 29 supplies a signal to eddy current exciting winding 5. Echoes from test piece 2 are received via receiving winding 3. Through an active adapter means 4 the signals are coupled to a display amplifier 30 and then to a display 31. The total operation is activated by a control 32. The magnetic field is controlled via a direct current source 33.

Figure 2:
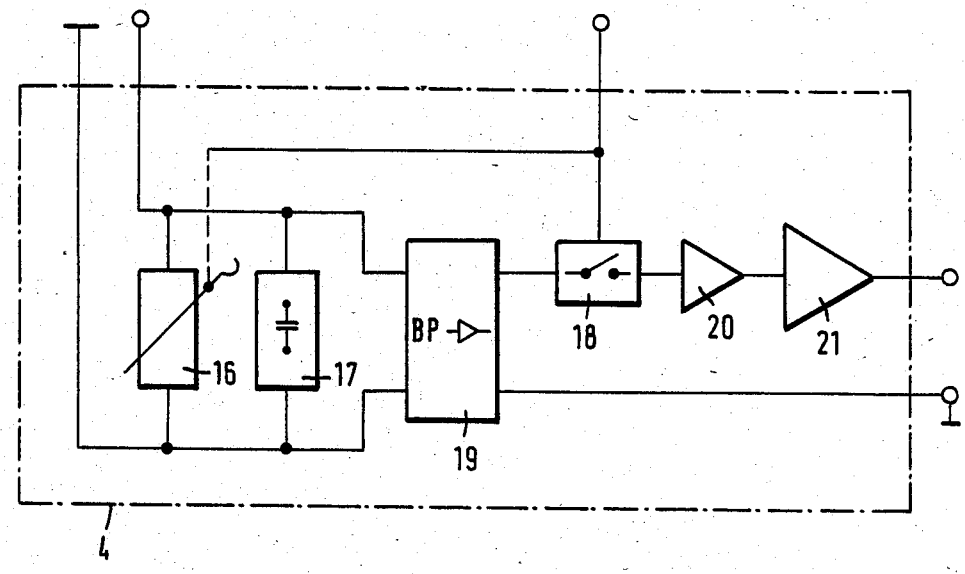
FIG. 2 is a more detailed schematic diagram of adapter member 4, shown in block diagram form in FIG. 1.

Referring now specifically to FIG. 2, active adapter means 4 of electronic signal processing unit 23 preferably comprises an electronically controllable damping means 16, adapter means 17, a transmit-receive switch 18, a band-pass filter 19, a pre-amplifier 20 and a line driver 21. Adapter means 17 comprises one or more matching capacitors.

The signals from receiving winding 3 are scanned by adapter means 17, transferred via the pre-amplifier 20 and thereafter via a line driver 21 to a line, which can be of any length in this configuration. To protect pre-amplifier 20 from overmodulating, there is provided a transmit-receive switch 18, essentially comprising an analog switch and diverse protective diodes.

The electronically controllable damping means 16 located in the input circuit forms a resonant circuit winding 3 and adapter means 17. Transmission can be damped to such an extent that there will be no inadmissibly long dead time during which echoes cannot be received. If for tolerance reasons the distance between EMT 1 and test piece 2 is changed, this may require a variation of the damping of the oscillatory circuit resulting in a longer transmitting dead time and a broadening of the echo pulses. A broadening of the echo pulses, however, would decrease resolution capacity. On the other hand, active adapter means 4 according to the invention provides an adequate damping of the transmit and echo signals. This is realized by electronically controllable damping means 16 and band-pass filter 19.

The following non-limitative examples represent typical embodiments of the instrument according to the invention:

EXAMPLE 1

| | |
|---|---|
| Test Piece: | Tube with a wall thickness of 40 mm |
| Material: | Ferritic steel |
| Temperature: | 1200° C. |
| Measurement: | Wall thickness |
| Transmitter: | Length of pulse 1 s at 300 V on 12 ohms |
| Transformer distance: | 1 mm (tolerance ± 0.5 mm) |
| Transformer windings: | Transmitter 20, 0.1 mm copper wire |
| | Receiver 50, 0.05 mm copper wire |
| Accuracy of measurement: | ± 0.1 mm |

EXAMPLE 2

| | |
|---|---|
| Test piece: | Aluminum band with a thickness of 20 mm |
| Temperature: | Ambient temperature |
| Measurement: | Thickness of band |
| Transmitter: | Pulse length 1 s at 300 V on 12 ohms |
| Transformer distance: | 0.85 mm (tolerance ± 0.3 mm) |
| Transformer windings: | Transmitter 29, 0.1 mm copper enamelled wire |
| | Receiver 50, 0.05 mm copper enamelled wire |
| Accuracy of measurement: | ± 0.05 mm |

The invention is not restricted to air as a working energy, and is also operating under a heavy radial load, e.g., in hot cells of nuclear plants.

While the invention has been described in connection with what is presently considered to be the most practical and preferred embodiment, it is to be understood that the invention is not to be limited to the disclosed embodiments but on the contrary, is intended to cover various modifications and equivalent arrangements included within the spirit and scope of the appended claims which scope it to be accorded the broadest interpretation so as to encompass all such modifications and equivalent structures.

We claim:

1. An instrument for testing a test piece made of a paramagnetic or diamagnetic metallic materials or ferromagnetic materials above its Curie point for material defects and/or dimensional accuracy, comprising:

an electromagnetic transducer (EMT) having an inner magnetic pole shoe tapered conically in the direction of the test piece and an outer magnetic pole shoe for together providing a magnetic field having substantial components parallel to said test piece, said first pole shoe comprising sheets extending substantially parallel to one another and insulated from one another, a heat-insulated eddy current exciting winding and a heat-insulated eddy current receiving winding;

an electronic signal processing unit, coupled to said EMT for analyzing signals received therefrom and generating data indicative thereof; and means for displaying said data in human readable form.

2. An instrument according to claim 1 wherein said instrument is positioned with respect to said test piece and arranged such that said eddy current exciting and receiving windings each have a side facing said test piece and a side facing away from said test piece, their respective sides facing the test piece being embedded in a heat-insulating ceramic layer and their respective sides facing away from said test piece being embedded in a heat-conducting ceramic layer.

3. An instrument according to claim 2 wherein said heat-insulating ceramic layer is made of aluminum oxide and wherein said heat-conductive coating is made of a ceramic adhesive.

4. An instrument according to claim 1 wherein said inner and outer pole shoes include respective pole shoe surfaces and the outer shoe is in the form of a hollow cylinder with a flat surface facing said test piece and wherein said second pole shoe is inclined at an angle of at least 25° with respect to a plane defined by said pole shoe surfaces.

5. An instrument according to claim 4 wherein said pole shoe surfaces are substantially at the same distance from the test piece and have the same surface dimensions.

6. An instrument according to claim 1 wherein said outer pole shoe has an edge surface and wherein the conical inclination of said inner pole shoe is substantially equal to the inclination of said edge surface of said outer pole shoe.

7. An instrument according to claim 6 wherein said outer pole shoe further includes a jacket surface and another edge surface.

8. An instrument according to claim 1 further including a cooler arranged at a lower face of said outer pole shoe.

9. An instrument according to claim 1 further including a pole shoe support for said inner pole shoe, said support including a cooling groove formed therein.

10. An instrument according to claim 1 wherein said electronic signal processing unit includes an active adaption means comprising:

damping means for damping a signal received from said eddy current receiving winding;

a capacitor for filtering said signal received from said eddy current receiving winding;

a filter for filtering said signal from said receiving winding;

a transmit/receive switch for selectively passing a signal from said filter;

a pre-amplifier for amplifying a signal passed by said switch; and a line driver for further amplifying a signal passed by said switch and amplified by said pre-amplifier.

* * * * *